United States Patent [19]

Manara et al.

[11] 4,038,337

[45] July 26, 1977

[54] PROCESS FOR ISOMERIZING ALKENES

[75] Inventors: Giovanni Manara; Vittorio Fattore; Bruno Notari, all of San Donato Milanese (Milan), Italy

[73] Assignee: Snam Progetti S.p.A., Milan, Italy

[21] Appl. No.: 601,208

[22] Filed: Aug. 1, 1975

[30] Foreign Application Priority Data

Aug. 2, 1974 Italy .................................. 25943/74

[51] Int. Cl.² .............................................. C07C 5/22
[52] U.S. Cl. .............................. 260/683.2; 252/455 R
[58] Field of Search .................. 260/683.2; 252/455 R

[56] References Cited

U.S. PATENT DOCUMENTS

| | | | |
|---|---|---|---|
| 2,242,387 | 5/1941 | Boyd | 260/683.2 |
| 2,280,054 | 6/1943 | Martin et al. | 260/683.2 |
| 2,300,151 | 10/1942 | Hemminger | 260/683.2 |
| 2,322,622 | 6/1943 | Fischer et al. | 260/683.2 |
| 2,328,753 | 9/1943 | Thomas | 260/683.2 |
| 2,483,131 | 9/1949 | Garrison | 260/683.2 |
| 3,213,156 | 10/1965 | Harding et al. | 260/683.2 |
| 3,345,428 | 10/1967 | McGrath et al. | 260/683.2 |
| 3,698,157 | 10/1972 | Allen et al. | 208/310 |

*Primary Examiner*—Veronica O'Keefe
*Attorney, Agent, or Firm*—Ralph M. Watson

[57] ABSTRACT

The invention relates to the skeleton isomerization of alkenes and, more particularly, to the catalyst for the isomerization reaction, the catalyst being prepared by treating an oxide of a metal of the group comprising aluminium, titanium, magnesium, silicon, chrome, zirconium, iron and their mixtures, preferably an active alumina, with a silicon compound, preferably an alkyl ester of the orthosilicic acid, and then subjecting the thus treated oxide to drying and to a controlled oxidation. Thus catalyst is obtained which permits higher yields and selectivity of the isomerization reaction to be achieved, as well as a longer operative life of the catalyst before the regeneration thereof.

21 Claims, No Drawings

PROCESS FOR ISOMERIZING ALKENES

The present invention relates to a process for isomerizing alkenes by using a particular catalyst.

The necessity to convert olefins having a linear chain into olefins having a branched chain and viceversa is often considered in the cycles treating particular oil cuts.

This is the case, for instance, of $C_4$ and $C_5$ cuts, wherefrom isobutene and isoamilenes are separated, for which there is the trend to convert the residual normal olefins into said products which are useful for reactants of polymerization, alkylation, disproportionating and so on.

On the contrary it can be interesting when the market of normal olefins requests it, to transform iso-olfins into normal olefins.

Many catalysts have been proposed for the aforesaid purpose including activated alumines such as eta- and gamma-alumina, halogenated alumines, bauxite, alumines treated with boron, zirconium and barium compounds, various silico-aluminates, more or less complex phosphates.

All the cited catalysts present some drawbacks such as, for instance, low selectivity of the desired reaction due to parallel or consecutive reactions of cracking and polymerization, to the quick lowering of the catalytic properties, to the regeneration difficulties, to the cost of the relevant materials which are rather rare, and so on.

It has been now surprisingly found that it is possible to carry out the skeleton isomerization of alkenes in a simple and economical way be means of a highly active catalyst, stable in the time and easily regenerable.

Object of the present invention is a process for the skeleton isomerization of alkenes consisting in contacting the alkene with a catalyst obtained by reacting an active alumina, preferably gamma- or eta-alumina, with an ester of the silicic acid, as described in co-pending U.S. patent application Ser. No. 519,792 filed Oct. 31 1974, in the name of the same Applicant.

According to the aforesaid application it is possible to improve the mechanical properties of materials constituted by metallic oxides by treating said materials with a silicon compound and subjecting the product so obtained to drying and to a controlled oxidation.

Utilizable silicon compounds have as general formula

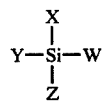

wherein X, Y, Z and W can by —R, —OR, —Cl, —Br, —SiH$_3$, —COOR, —SiH$_n$Cl$_m$, R being either hydrogen, or an alkyl, cycloalkyl, aromatic, alkyl aromatic, alkylcycloalkyl radical having from 1 to 30 caron atoms such as for instance methyl, ethyl, isopropyl, n-propyl, n-butyl, isobutyl, cyclohexyl, cyclopentyl, phenyl, phenyl cyclohexyl or alkylphenyl radical, n and m being whole numbers in the range from 1 to 3.

Among the cited compounds preferred are the esters of the orthosilicic acid such as for instance the methyl, ethyl, propyl, isopropyl, isobutyl and n-butyl tetrasilicates.

The materials which can be treated according to the aforesaid procedure are all the oxides, in particular aluminium oxides, titanium oxides, magnesium oxides, silica, chrome oxides, zirconium oxides, iron oxides an mixtures of said oxides among them or with other compounds.

It has been now found that, in the particular case of aluminas, the above-mentioned treatments render them more active and selective for the skeleton isomerization of alkenes.

The catalyst obtained in such a way is highly resistant to the hydrothermic conditions present during regenerations with air, since the silicon surface layer, which forms by reaction of the surface -OH groups of alumina and the ester of silicic acid, improves the resistance to the synthesization of (gamma and eta) alumina. This leads to a longer duration of such catalysts in comparison with the conventional ones and to an increased economy in the plant.

The secondary reactions of cracking and polymerization are moderate and the loss of activity of the catalyst, between a regeneration and the following one, is slower than that of the catalysts up to now used for isomerization reactions.

The catalyst is prepared so as to deposit on the alumina surface from 0.5% to 12% by weight of silica and preferably, from 1% to 7%, based on the total final weight of the catalyst.

Various preparation methods can be used as described in the U.S. Patent Application in the name of the same Applicant already cited.

The skeleton isomerization process according to the present invention can be carried out by contacting the alkene or the alkene mixture, possibly also in presence of alkanes or other inert gases such as nitrogen or $CO_2$, with the catalyst at a temperature in the range of from 300 to 600° C and preferably from 400° to 550° C. The reaction pressure can be selected among the ones more convenient for the particular alkene or mixture of treated hydrocarbons but generally it is in the range of from the atmospheric pressure to 10 Atm.

The feed space velocity expresed as W.H.S.V. can range from 0.1 to 20 and preferably from 0.2 to 10.

EXAMPLE 1

The present Example relates to the preparation of the catalyst according to the teachings of U.S. patent application Ser. No. 519,792

100 g of alumina were put in autoclave together with 20 g of $(C_2H_5O)_4Si$. The autoclave was evacuated and washed many times with gaseous $N_2$ in order to eliminate any $O_2$ trace; at last it was brought to a pressure of 5 kg/cm$^2$ with $N_2$.

The autoclave was heted to 200° C and maintained at this temperature for 4 hours. At last it was cooled, the pressure was lowered and the alumina was recovered; the alumina was subjected to a subsequent thermal treatment 2 hours long at 200° C in presence of nitrogen and then to a calcination in air at 500° C for 4 hours.

The gamma-$Al_2O_3$ spherules treated as described, revealed at the analysis a $SiO_2$ content equal to 5.6% by weight.

The alumina samples treated as described were utilized for the test of catalytic activity in the skeleton isomerization of alkenes, as will be better indicated in the subsequent examples.

EXAMPLE 2

A commercial gamma-alumina in spherules of about 3-4 mm diameter, the properties of which are reported in Table 1, was dried in a nitrogen stream at 450° C.

For comparative purposes a portion of said alumina was utilized as such while a second portion was treated with tetraethylorthosilicate with the procedure and doses reported in in Example 1, so that the content of silica on the alumina was 5.6%.

Each one of the two catalysts was put in a fixed bed tubular reactor having a volume of 20 cm³.

The C₄ feed was passed over the catalytic bed at 492° C and at atmospheric pressure with a space velocity of about 1.70 (g|g×h).

The effluent stream from the reactor, after condensation at room temperature of the C₅ products, was analyzed by gaschromotography. The analysis of the effluent stream gave the compositions by weight reported in Table 3.

TABLE 3

COMPOSITION OF THE EFFLUENT STREAM FROM THE REACTOR AFTER ISOMERIZATION

| Catalyst | Alumina A | | | Alumina A + 5.6 % SiO₂ | | |
|---|---|---|---|---|---|---|
| Running hours | 1.5 | 3.5 | 2.25 | 4 | 6 | 8 |
| Space velocity(g/g×h) | 1.72 | 1.70 | 1.66 | 1.66 | 1.76 | 1.83 |
| C₂ – C₃ hydrocarbons | 1.74 | 1.10 | 3.38 | 3.36 | 3.18 | 2.99 |
| isobutane | 2.96 | 3.13 | 3.26 | 3.21 | 3.15 | 3.10 |
| n-butane | 15.83 | 16.21 | 16.99 | 16.75 | 16.59 | 16.43 |
| trans-butene 2 | 26.72 | 27.92 | 21.70 | 21.90 | 23.75 | 25.10 |
| isobutene | 9.11 | 6.87 | 20.77 | 19.00 | 15.73 | 13.73 |
| butene 1 | 18.50 | 19.75 | 14.57 | 15.05 | 16.59 | 16.80 |
| Cis-butene 2 | 22.34 | 22.94 | 17.01 | 18.73 | 19.65 | 20.57 |
| C₅ + hydrocarbons | 2.80 | 2.08 | 2.32 | 2.00 | 1.36 | 1.28 |

TABLE 1

CHARACTERISTICS OF SPHEROIDAL GAMMA-ALUMINA A

| packed bulk density | = | 0.51 g/cm³ |
| surface area (BET) | = | 301 m²/g |
| total volume of the pores | = | 0.879 cm³/g |
| Na₂O | = | 0.07 % |

$$\text{Conversion \%} = \frac{[(\epsilon\ BT\%)\text{in} - (\epsilon\ BL\%)\text{out}] \times 100}{(\epsilon\ BT\%)\text{in}}$$

$$\text{Selectivity to isobutene \%} = \frac{(\text{isobutene \%})\text{out} \times 100}{[(\epsilon\ BT\%)\text{in} - (\epsilon\ BL\%)\text{out}]}$$

$$\text{Yield to isobutene \%} = \frac{\text{Conversion \%} \times \text{Selectivity \%}}{100}$$

$$= \frac{(\text{Isobutene \%})\text{out} \times 100}{(\epsilon\ BT\%)\text{in}}$$

$$\text{Yield to} <C_4 + \text{saturated hydrocarbons \%} = \frac{[(<C_4 + \text{Saturated hydrocarbons \%})\text{out} - (<C_4 + \text{Saturated hydrocarbons \%})\text{in}] \times 100}{(\epsilon\ BT\%)\text{in}}$$

$$\text{Yield to } C_5 + \text{hydrocarbons} = \frac{(C_5+)\text{out} \times 100}{(\epsilon\ BT\%)\text{in}}$$

This catalyst as well as a portion of the not silicized alumina was subjected to skeleton isomerization tests of a C₄ feed having the composition by weight reported in Table 2.

TABLE 2

COMPOSITION OF C₄ OLEFINIC FEED

| C₂ – C₃ hydrocarbons | 0.37 % |
| iso-butane | 3.23 % |
| n-butane | 16.51 % |
| trans-butene 2 | 14.03 % |
| isobutene | 1.50 % |
| butene 1 | 64.36 % |

Data above reported show how the treatment with tetraethylorthosilicate has more than doubled the amount of isobutene leaving the catalytic reactor.

For effecting comparisons use was made of the following definitions:

The above reported symbols have the following meaning:

Σ Bl = Σ Linear Butenes = Trans-butene 1 + Butene 1 + cis-butene 2

Σ BT = Σ Total Butenes = Trans-butene 2 + Butene 1 + cis-butene 2 + isobutene

<C₄ + Saturated hydrocarbons = C₁, C₂ and C₃ hydrocarbons = Isobutene + Butene

C₅⁺ products with 5 or more carbon atoms.

Symbols in and out means respectiely introduced into and discharged from the reactor. By using said definitions we have summarized in Table 4 the catalytic behaviour before and after the treatment with tetraethylorthosilicate.

TABLE A

SUMMARIZING TABLE FOR ISOMERIZATION

| Catalyst | Alumina A | | | Alumina A + 5.6% SiO₂ | | |
|---|---|---|---|---|---|---|
| Running hours | 1.5 | 3.5 | 2.25 | 4 | 6 | 8 |
| Speed velocity (g/g×h) | 1.72 | 1.70 | 1.66 | 1.66 | 1.76 | 1.83 |
| Conversion % by weight | 15.4 | 11.6 | 33.3 | 30.3 | 24.9 | 21.8 |
| Selectivity to isobutene % by weight | 73.9 | 74.1 | 78.1 | 78.5 | 79.1 | 78.9 |
| Yield to Isobutene % by weight | 11.4 | 8.6 | 26.0 | 23.8 | 19.7 | 17.2 |
| Yield <C₄ + saturated | | | | | | |

TABLE A-continued

| SUMMARIZING TABLE FOR ISOMERIZATION | | | | | | |
|---|---|---|---|---|---|---|
| Catalyst | Alumina A | | | Alumina A + 5.6% SiO$_2$ | | |
| hydrocarbons % by weight | 0.5 | 0.4 | 4.4 | 4.0 | 3.5 | 3.0 |
| Yield to C$_5$+ % by weight | 3.5 | 2.6 | 2.9 | 2.5 | 1.7 | 1.6 |

It is immediately evident how the modification consequent the treatment with silicon derivatives makes more than double the conversion of linear butenes, increasing contemporaneously the selectivity.

The yield to isobutene which was 11.4% in presence of the not treated alumina rises to 26% in presence of the silicized alumina. Moreover the activity fall due to the aging results to be slower.

EXAMPLE 3

100 g of a spheroidal commercial gamma-alumina B having the characteristics listed in Table 5 were treated with 20 g of tetraethylorthosilicate according to the procedures described in Example 1 so that the silica content in the final product was 5%.

TABLE 5

| CHARACTERISTICS OF SPHEROIDAL GAMMA-ALUMINA B | | |
|---|---|---|
| Packed bulk density | = | 0.77 g/cm$^3$ |
| Surface area | = | 360 m$^2$/g |
| Total volume of the pores | = | 0.50 cm$^3$/g |
| Na$_2$O | = | 0.6 % |

For comparative purposes this alumina with 5% silica and the same alumina but not treated were tested for the isomerization by utilizing the feed described in Table 2 and the apparatus described in Example 2. By using the same calculation scheme and by working at atmospheric pressure at 492° C with a space velocity of about 0.77 g/gxh and a catalytic bed of 20 cc the results reported in Table 6 were obtained.

TABLE 6

| ISOMERIZATION OF A C$_4$ OLEFINIC FEED STREAM | | | | |
|---|---|---|---|---|
| Catalyst | Alumina B | | Alumina B + 5% SiO$_2$ | |
| Running hours | 1.5 | 3.5 | 1.5 | 3.5 |
| Space velocity (g/g×h) | 0.78 | 0.81 | 0.74 | 0.77 |
| Conversion % by weight | 17.0 | 11.3 | 27.8 | 23.0 |
| Selectivity % by weight | 72.5 | 75.0 | 75.9 | 75.5 |
| Yield to isobutene % by weight | 12.3 | 8.5 | 21.1 | 17.4 |
| Yield to < C$_4$ + % by weight saturated hydr- % by weight | 1.8 | 0.7 | 3.1 | 2.4 |
| Yield to C$_5$ + % by weight | 2.9 | 2.1 | 3.6 | 3.2 |

It is possible to see how the modification consequent the treatment with silicon derivatives causes a strong increase of conversion so that the yield to isobutene passes from 12.3 to 21.1% after 1.5 hours and from 8.5 to 17.4% after 3.5 hours.

These data show that silicization keeps in the time its positive effect and causes the dual effect of increasing the catalyst activity and prolong duration in the time.

EXAMPLE 4

A commercial gamma-alumina having the properties listed in Table 7 was partially utilized as such for comparative purposes and, partially, treated with variable amounts of tetraethylortho silicata.

100 g of such alumina were treated with 5 g of tetraethylorothosilicate obtaining a finished catatlyst containing 1.6% of silica while 100 g of the same alumina were treated with 10 g of tetraethylorthosilicate, obtaining a finished catalyst containing 2.9% of silica.

TABLE 7

| PROPERTIES OF A GAMMA-ALUMINA C | | |
|---|---|---|
| Packed bulk density | = | 0.55 g/cm$^3$ |
| Surface area | = | 169 m$^2$/g |
| Total volume of the pores | = | 0.56 cm$^3$/g |
| Na$_2$O | = | <20 ppm |

The three catalysts, obtained as described, were subjected to tests of skeleton isomerization of the C$_4$ feed the composition of which is reported in Table 2, by working at atmospheric pressure and at 465° C, in a heated tubular reactor having a fixed bed of 50 cm$^3$.

The data concerning the three catalysts are summarized in Table 8.

TABLE 8

| ISOMERIZATION OF A C$_4$ OLIFINIC FEED STREAM | | | |
|---|---|---|---|
| Catalyst | Alumina C | Alumina C + 1.6% SiO$_2$ | Alumina C + 2.9% SiO$_2$ |
| Temperature ° C | 465 | 465 | 465 |
| Running hours | 2 | 2.5 | 4 |
| Space velocity g/g×h | 0.47 | 1.31 | 1.29 |
| Conversion % by weight | 35.6 | 34.3 | 36.0 |
| Selectivity to isobutene % by weight | 63.4 | 73.2 | 77.0 |
| Yield to isobutene % by weight | 22.6 | 25.1 | 27.7 |
| Yield to <C$_4$+ saturated hydrocarbons % by weight | 7.2 | 5.6 | 5.5 |
| Yield to C$_5$+ % by weight | 5.8 | 3.6 | 2.8 |

It is clearly evident how silicization of gammalumina C increases the catalyst activity which reaches the same conversion at a space velocity 2.5 times higher than that of the not silicized alumina.

There is furthermore a positive effect on selectivity which is increased of 10 – 15 points and a positive effect on the life.

In fact the material containing 2.9% SiO$_2$ maintains after 4 hours, at a space velocity 2.5 times higher, an activity higher than that shown, after 2 hours, by the not treated catalyst.

EXAMPLE 5

The same alumina of Example 4 containing 1.6% of $SiO_2$ and, for comparative purposes, the same not silicized alumina were utilized for the isomerization of pure transbutene 2, by working at 485° C and atmospheric pressure with a catalytic bed of 50 cm³.

The results of isomerization are reported in Table 9.

TABLE 9
ISOMERIZATION OF TRANS-BUTENE 2

| Catalyst | Alumina C | Alumina C + 1.6 % $SiO_2$ |
|---|---|---|
| Temperature ° C | 485 | 485 |
| Running hours | 2 | 2.5 |
| Space velocity (g/g×h) | 0.54 | 1.81 |
| Conversion % by weight | 25.6 | 34.3 |
| Selectivity to isobutene % by weight | 67.2 | 71.8 |
| Yield to isobutene % by weight | 17.2 | 24.6 |
| Yield to <$C_4$ + saturated hydrocarbons % by weight | 5.3 | 8.0 |
| Yield to $C_5$+ % by weight | 3.1 | 1.7 |

The space velocity at which the silicized catalyst worked was three times higher and, notwithstanding this, the conversion and selectivity obtained thereon were higher.

Over the same catalysts the isomerization of transbutene 2 was carried out at 515° C and atmosphere pressure with a catallytic bed of 50 cm³. The data of isomerization are listed in Table 10.

It is to be noted that at said temperature alumina as such loses 13 points of selectivity, while alumina containing 1.6% $SiO_2$ loses only 2 points of selectivity. This demonstrates that the silicized catalyst works in a wider temperature range with the comsequent advantages on the velocity of the isomerization reaction and therefore on the size of the plants without excessive losses in undesired products.

it is to be noted that the space velocity at which silicized alumina works is four times higher than that at which not treated alumina works.

TABLE 10
ISOMERIZATION OF TRANS-BUTENE 2

| Catalyst | Alumina C | Alumina C + 1.6% $SiO_2$ |
|---|---|---|
| Temperature ° C | 515 | 515 |
| Running hours | 1 | 1 |
| Space velocity (g/g×h) | 0.65 | 2.6 |
| Conversion % by weight | 26.9 | 33.3 |
| Selectivity % by weight | 54.2 | 69.6 |
| Yield to isobutene % by weight | 14.6 | 22.3 |
| Yield to <$C_4$+ saturated hyd. % by weight | 7.8 | 8.5 |
| Yield $C_5$+ % by weight | 4.5 | 1.6 |

EXAMPLE 6

100 g of commercial alumina D the properties of which are reported in Table II were treated with 20 g of tetraethylorthosilicate according to the procedure described in Example 1 so that the content of silica in the finished catalyst was 4.8%.

TABLE 11
CHARACTERISTICS OF GAMMA-ALUMINA D

| | |
|---|---|
| Packed bulk density | 0.95 g/cm³ |
| Surface area | 210 m²/g |
| Total volume of the pores | 0.40 cm³/g |
| $Na_2O$ | 0.8 % |

The not treated alumina and the alumina containing 4.8% of $SiO_2$ were utilized for the isomerization of the $C_4$ olefinic feed having the composition reported in Table 2, by working at atmosphere pressure and at 492° C in a fixed bed reactor of 20 cm³.

The results of the catalytic tests are reported in Table 12.

It is to be noted how the catalyst containing silica at the same space velocity as that used for the catalyst without silica offers a conversion of 27–28% vs. 5.7 – 5.8% so that the yield to isobutene passes from 4% to 17%.

Also an alumina which as such does not present any isomerizing activity, by treatment with tetraethylorthosilicate can therefore become an effective isomerization catalyst.

TABLE 12
ISOMERIZATION OF A $C_4$ OLEFINIC FEED

| Catalyst | Alumina D | | Alumina D + 4.8% $SiO_2$ | |
|---|---|---|---|---|
| Temperature ° C | 492 | 492 | 492 | 492 |
| Running hours | 1 | 3 | 1 | 3 |
| space velocity (g/g×h) | 0.45 | 0.40 | 0.49 | 0.44 |
| Conversion % by weight | 5.8 | 5.7 | 27.9 | 27.4 |
| Selectivity % by weight | 69.2 | 69.9 | 61.9 | 60.0 |
| Yield to isobutene % by weight | 4.0 | 4.0 | 17.3 | 16.4 |
| Yield to <$C_4$+ saturated hydrocarbons % by weight | 0.5 | 0.5 | 6.5 | 7.2 |
| Yield to $C_5$+ % by weight | 1.3 | 1.2 | 4.1 | 3.8 |

EXAMPLE 7

A commercial gamma-alumina in the form of extruded alumina having a diameter of 1.5 mm constitutes alumina E, the properties of which are reported in Table 13.

TABLE 13
PROPERTIES OF GAMMA-ALUMINA E

| | | |
|---|---|---|
| Packed bulk density | = | 0.72 g/cm³ |
| Surface area | = | 349 m²/g |
| Total volume of the pores | = | 0.60 cm³/g |
| $Na_2O$ | = | 40 ppm |

Such alumina was divided in 4 portions of 100 g each which were treated respectively with 5, 10, 13 and 18 g of tetraethylorthosilicate, according to the procedure reported in Example 1 so that 4 catalysts were obtained containing respectively 1.5%, 2.4%, 3.5%, and 8.2% of $SiO_2$.

The 4 catalysts were utilized for the isomerization of the $C_4$ feed the composition of which is reported in Example 2, by working in a fixed bed reactor of 50 cm³ at atmospheric pressure.

The results of the catalytic tests carried out at temperatures in the range of from 456° to 492° C are reported in Table 14.

It is immediately possible to note the high selectivity values obtained with the different catalysts, with the exception of the one containing 8.2% of silica which catalyst is very active but offers modest selectivities. This demonstrates that the best results in the isomerization of $C_4^+$ olefins are obtained when the amount of Conversion % = $[100 - (\text{isobutene \%})_{out}]$ Selectivity to linear butens % = $\dfrac{(\Sigma\ BL\ \%)_{out} \times 100}{100 - (\text{isobutene \%})_{out}}$ Yield to linear butenes = $\dfrac{\text{Conversion \%} \times \text{Selectivity \%}}{100} = (\Sigma\ BL\ \%)_{out}$ Yield to $C_4$ + saturated hydrocarbons = $(< C_4 + \text{Saturated hydrocarbons \%})_{out}$ Yield to $C_5+$ = $(C_5 +)_{out}$

TABLE 14

ISOMERIZATION OF A $C_4$ OLEFINIC STREAM

| Catalyst | Alumina E +1.5% SiO$_2$ | | Alumina E +2.4% SiO$_2$ | | Alumina E +3.5% SiO$_2$ | | Alumina E +8.2% SiO$_2$ | |
|---|---|---|---|---|---|---|---|---|
| Temperature ° C | 474 | 474 | 456 | 492 | 492 | 492 | 465 | 465 |
| Running Hours | 1 | 2.5 | 1.5 | 1.5 | 4 | 5.5 | 1 | 2.5 |
| Space velocity (g/g×h) | 1.60 | 1.57 | 1.53 | 2.09 | 2.24 | 2.35 | 2.32 | 2.07 |
| Conversion % by w. | 42.5 | 39.6 | 37.4 | 41.4 | 36.6 | 33.6 | 47.2 | 43.7 |
| Selectivity % by w. | 77.5 | 79.0 | 78.9 | 78.9 | 83.1 | 78.4 | 59.4 | 64.9 |
| Yield to isobutene % by w. | 32.9 | 31.3 | 29.5 | 32.7 | 30.4 | 26.3 | 28.0 | 28.4 |
| Yield <$C_4$+ saturated hydrocarbons % by w. | 5.8 | 4.8 | 3.9 | 4.7 | 3.8 | 5.2 | 8.7 | 5.6 |
| Yield to $C_5$+ % by w. | 3.8 | 3.5 | 4.0 | 4.0 | 2.4 | 2.1 | 10.5 | 9.7 | silica introduced on the catalyst is in the range of from 1% to 7%, while for amounts of 8 – 12% there is a high activity and a modest selectivity.

EXAMPLE 8

A sample of the gamma-alumina E containing 1.5% of SiO$_2$ described in Example 7, was subjected to a test of duration in the time, by working in fixed bed with 20 cc of catalyst at a temperature of 460° C with the $C_4$ stream described in Table 2.

The results reported in Table 15 show how to catalyst maintains the yield at values higher than 30% for a very prolonged time so that the periodic regenerations, which for the catalysts known in the art are necessary after working periods of 3-5 hours can be effected at longer intervals of 15 – 20 hours.

TABLE 16

ISOMERIZATION OF ISOBUTENE TO LINEAR BUTENES OVER GAMMA-ALUMINA C + 1.6 % SiO$_2$

| | | 465 | 465 |
|---|---|---|---|
| Temperature ° C | | 465 | 465 |
| Running hours | | 1 | 1 |
| Space velocity (g/g×h) | | 1 | 0.6 |
| Conversion | % by weight | 43.4 | 56.4 |
| Selectivity to linear butenes | " | 87.1 | 78.4 |
| Yield to linear butenes | " | 37.8 | 44.2 |
| Yield to < $C_4$ + saturated hydroc. | " | 3.6 | 8.2 |
| Yield to $C_5$ + | " | 2.0 | 4.0 |

It is possible to note the high conversion and the high selectivity which have been obtained in the reaction and

TABLE 15

ISOMERIZATION OF $C_4$ OLEFINIC FEED OVER ALUMINA E

| Temperature ° C | 460 | 460 | 460 | 460 | 460 | 460 | 460 | 460 | 460 |
|---|---|---|---|---|---|---|---|---|---|
| Running hours | 1 | 3 | 5 | 7 | 11 | 13 | 14.5 | 16.5 | 18 |
| Space velocity (g/g×h) | 0.86 | 0.82 | 0.82 | 0.83 | 0.76 | 0.73 | 0.75 | 0.76 | 0.74 |
| Conversion % by w. | 49.4 | 48.4 | 47.5 | 46.0 | 43.0 | 42.2 | 41.3 | 40.7 | 38.7 |
| Selectivity % by w. | 74.8 | 75.9 | 75.8 | 76.8 | 76.9 | 77.0 | 76.9 | 77.2 | 77.9 |
| Yield to isobutene % by w. | 37.0 | 36.7 | 36.0 | 35.3 | 33.1 | 32.5 | 31.8 | 31.4 | 30.1 |
| Yield to <$C_4$+sat. hydrocarbons % by w. | 8.3 | 7.4 | 7.2 | 6.9 | 6.3 | 6.2 | 6.1 | 6.1 | 5.9 |
| Yield to $C_5$+ % by w. | 4.1 | 4.3 | 4.3 | 3.8 | 3.6 | 3.5 | 3.4 | 3.2 | 2.7 |

EXAMPLE 9

100 g of commercial gamma-alumina C the properties of which are reported in Table 7 were treated with 5 g of tetraethylorthosilicate according to the procedure described in Example 1.

The catalyst obtained in such a way, containing 1.6% of silica, was utilized for the skeleton isomerization reaction of isobutene to linear butenes.

By feeding a stream constituted by pure isobutene at a temperature of 465° C over a catalytic bed of 20 cm$^3$ and respectively at a space velocity of 1 and 0.6 (g/gxh) we obtained after 1 hour of run the results reported in Table 16.

Linear butenes obtained were constituted for 45-46& by trans-butene 2, for 27-28% by butene and for 10-12% by cis-butene 2.

The results are expressed by the following formulae:

this shows the capability of the catalysts object of the present invention to carry out with excellent yields the isomerization reaction of isobutene to linear butenes.

EXAMPLE 10

Pure trans-butene 2 was made flow for 24 hours at 492° C over alumina A and over the same alumina containing 5.6% of SiO$_2$, already described in Example 2.

After such time period the isomerizing activity became practically zero because of the deposit of carbonaceous products on the catalysts.

The two catalysts were subsequently subjected to regeneration by feeding a quantity of air such that the combustion of the carbonaceous products took place in a very short time; at these conditions the temperature of the gas contacting the catalyst reached 900° C.

Generally the regeneration of the catalysts deactivated by carbonaceous deposits is carried out in such a way that the temperature of the gases contacting the catalyst does not exceed the temperature of 600°–650° C.

However, such procedure is very slow and lowers the time of utilization of the plant.

A quicker procedure can present advantages for the running of the plant.

In any case this drastic treatment can reveal the behaviour of the materials when repeated low temperature regenerations are effected.

Over the catalysts so regenerated there was effected a test of isomerization of trans-butene 2 at 492° C obtaining the results reported in Table 17.

The practically nonexistent conversion of transbutene 2 over alumina A relates to the non-formation of isobutene, cracking or alkylation products, according to the definitions reported in Example 2, while it was observed the formation of linear butenes, butene 1 and butene 2-cis.

The activity of alumina containing 5.6% of silica remains on the contrary very good also after the regeneration carried out in drastic conditions.

TABLE 17
ISOMERIZATION OF TRANS-BUTENE 2

| Catalyst | Alumina A after regeneration | Alumina A + 5.6% SiO$_2$ after regeneration |
|---|---|---|
| Temperature ° C | 492 | 492 |
| Space velocity (g/g×h) | 1.30 | 1.28 |
| Running hours | 1.5 | 1.5 |
| Conversion by weight | < 0.5 | 28.8 |
| Selectivity % by weight | — | 72.2 |
| Yield to isobutene % by weight | traces | 20.8 |
| Yield to <C$_4$+ saturated hydrocarbons % by weight | nonexistent | 5.3 |
| Yield to C$_5$+ % by weight | nonexistent | 2.7 |

EXAMPLE 11

Over the gamma-alumina E catalyst containing 3.5% of silica described in Example 7 we fed pure pentane, by working in a tubular reactor containing a catalytic bed of 20 cm$^3$ at atmospheric pressure and at a temperature of 420° and 450° C.

The effluent stream from the reactor contained besides linear pentenes isopentenes which can consider the useful reaction products and minor amounts of cracking products (<C$_5$) and alkylation products (C$_6$+).

For expressing more clearly the results we utilized the following definitions:

Conversion % $= 100 - (\Sigma \, PL \, \%)_{out}$

Selectivity to isopentenes % $= \dfrac{(\Sigma \, IP \, \%)_{out} \times 100}{100 - (\Sigma \, PL \, \%)_{out}}$ Yield to isopentenes % $= \dfrac{\text{Conversion \% } \times \text{ selectivity \%}}{100} = (\Sigma \, IP \, \%)_{out}$ Yield to < C$_5$ % $= (< C_5 \%)_{out}$
Yield to C$_6$ + $= (C_6 + \%)_{out}$ The above reported symbols have the following meanings:
$\Sigma$ PL = $\Sigma$ Linear Pentenes = Pentene 1 + Cis-pentene 2 + trans-pentene 2
$\Sigma$ IP = $\Sigma$ Branched Isopentenes = 2 Methul-butene 1 + 3 methyl-butene 1 + 2 methyl-butene 2
<C$_5$% = C$_1$ + C$_2$ + C$_3$ + C$_4$ saturated and unsaturated hydrocarbons
C$_6$+ = products with 6 and more carbon atoms.
out = means leaving the reactor In Table 18 we report the results of the tests we carried out.

TABLE 18
ISOMERIZATION OF PENTENE 1

| Temperature ° C | 420 | 450 |
|---|---|---|
| Space velocity (g/g×h) | 4 | 10 |
| Conversion % by weight | 40.8 | 37.8 |
| Selectivity % by weight | 74.7 | 72.9 |
| Yield to isopentenes % by weight | 30.5 | 27.6 |
| Yield to <C$_5$ % by weight | 3.5 | 2.4 |
| Yield to C$_6$+ % by weight | 6.8 | 7.8 |

It is clear how silicized alumina constitutes a valid catalyst for the isomerization reaction of linear pentenes to isopentenes.

EXAMPLE 12

A fraction of gasoline obtained by cracking boiling in the range of from 75° to 150° C, containing alkenes having a number of carbon atoms higher than 5 and having a research octane number (RON) of 86.5 for the product without lead alkyls was made to flow at 410° C over the catalyst constituted by gamma-Al$_2$O$_3$C + 1.6% SiO$_2$ described in Example 5. A yield to liquid products of 96% was obtained with formation of 0.3% of coke and 3.7% of light products.

The research octane number (RON) for the reaction product without lead alkyls was 90.1, obtaining therefore an improvement of 3.6 RON.

This improvement is due to the skeleton isomerization of the alkenes having a number of carbon atoms higher than 5, contained in the product subjected to isomerization.

What we claim is:

1. A process for the skeleton isomerization of alkenes which comprises contacting an alkene having at least four carbon atoms or a mixture of alkenes having at least four carbon atoms with a catalyst consisting essentially of alumina previously treated with a silicon compound having the formula

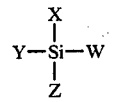

wherein X, Y, Z and W are selected from the group of —R, —OR, —Cl, —Br, —SiH$_3$, —COOR, —SiH$_n$Cl$_m$, R being either hydrogen or an alkyl, cycloalkyl, aromatic, alkyl-aromatic or alkyl-cycloalkyl radical having from 1 to 30 carbon atoms, n and m being whole numbers in the range of from 1 to 3.

2. The process of claim 1 wherein R is a methyl, ethyl, isopropyl, n-propyl, n-butyl, isobutyl, cyclohexyl, cyclopentyl, phenyl, phenyl cyclohexyl or alkylphenyl radical.

3. The process of claim 2 wherein R is a methyl, ethyl, n-propyl, isopropyl, isobutyl or n-butyl radical.

4. The process of claim 1 wherein the silicon compound is selected from the group of the methyl, ethyl, n-propyl, isopropyl, isobutyl and n-butyl tetrasilicates.

5. The process of claim 4 wherein the silicon compound is tetraethylorthosilicate.

6. The process of claim 1 wherein the alumina has deposited thereon from 0.5 to 12% of silica, based on the total weight of the catalyst.

7. A process of claim 6 wherein the alumina has deposited thereon from 1 to 7% of silica, based on the total weight of the catalyst.

8. The process of claim 1 wherein the process is carried out at temperatures in the range of from 300° to 600° C.

9. The process of claim 8 wherein the process is carried out at temperatures in the range of 400° to 550° C.

10. The process of claim 1 wherein the process is carried out at a pressure ranging from one to ten atmospheres.

11. The process of claim 1 wherein the process is carried out at a feeding space velocity ranging from 0.1 to 20.

12. The process of claim 11 wherein the process is carried out at a feeding space velocity ranging from 0.2 to 10.

13. The process of claim 1 wherein the alkene is butene, in a gas mixture consisting essentially of butene.

14. The process of claim 1 wherein the alkene is pentene, in a gas mixture consisting essentially of pentane.

15. A process for the skeleton isomerization of alkenes which comprises contacting an alkene having at least four carbon atoms or a mixture of alkenes having at least four carbon atoms with a catalyst consisting essentially of alumina previously treated with a silicon compound having the formula

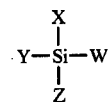

wherein X, Y, Z and W are selected from the group of —R, —OR, —Cl, —Br, —SiH$_3$, —COOR, —SiH$_n$Cl$_m$, R being either hydrogen or a methyl, ethyl, isopropyl, n-propyl, n-butyl, isobutyl, cyclohexyl, cyclopentyl, phenyl, phenyl cyclohexyl or alkylphenyl radical having up to 30 carbon atoms, n and m being whole numbers in the range of from 1 to 3.

16. A process for producing isobutene which comprises contacting butene at temperatures of from 300° to 600° C and at a pressure of from one to ten atmospheres with a catalyst consisting essentially of alumina previously treated with tetraethylorthosilicate to deposit thereon silica in an amount of from 0.5 to 12% by weight based on the weight of the catalyst.

17. The process of claim 16 wherein the silica is deposited in an amount of from 1 to 7% by weight based on the total weight of the catalyst.

18. A process for producing linear butenes which comprises contacting isobutene at a temperature of from 300° to 600° C and at a pressure of from one to ten atmospheres with a catalyst consisting essentially of alumina previously treated with tetraethylorthosilicate to deposit thereon silica in an amount of from 0.5 to 12% by weight based on the weight of the catalyst.

19. The process of claim 18 wherein the silica is deposited in an amount of from 1 to 7% by weight based on the total weight of the catalyst.

20. A process for producing isopentenes which comprises contacting pentene at a temperature of from 300° to 600° C and at a pressure of from one to ten atmospheres with a catalyst consisting essentially of alumina previously treated with tetraethylorthosilicate to deposit thereon silica in an amount of from 0.5 to 12% by weight based on the weight of the catalyst.

21. The process of claim 20 wherein the silica is deposited in an amount of from 1 to 7% by weight based on the total weight of the catalyst.

* * * * *